United States Patent [19]

Telford

[11] Patent Number: 4,529,057
[45] Date of Patent: Jul. 16, 1985

[54] EAR DEFENDERS
[75] Inventor: Peter Telford, Cheshire, England
[73] Assignee: The Marconi Company Limited, England
[21] Appl. No.: 484,185
[22] Filed: Apr. 12, 1983
[30] Foreign Application Priority Data Apr. 13, 1982 [GB] United Kingdom ................ 8210622

[51] Int. Cl.³ .............................................. H04R 25/00
[52] U.S. Cl. ................................. 181/129; 179/156 R; 179/182 R; 128/152
[58] Field of Search .............................. 181/129, 137; 179/156 R, 182 R; 128/152

[56] References Cited

U.S. PATENT DOCUMENTS 3,661,225  5/1972  Anderson ..................... 128/152 X
3,798,393  3/1974  Gorike ......................... 179/182 R
4,064,362 12/1977  Williams ..................... 179/182 R X Primary Examiner—John Gonzales
Assistant Examiner—Brian W. Brown
Attorney, Agent, or Firm—Kirschstein, Kirschstein, Ottinger & Israel

[57] ABSTRACT

An ear defender for a headset, the ear defender comprising a rigid shell having holes in a central portion to permit the passage of ambient sound and including a valve mechanism to close the holes as required. The shell consists essentially of a unitary construction, being formed as a one-piece moulding. The valve mechanism consists of a fixed plate and sliding plate both of which have holes which can be aligned to open the valve or misaligned to close the valve. The valve is mounted wholly within the shell so providing protection for the valve mechanism. Access to the valve and to other components within the shell is thus provided entirely from one side of the shell.

2 Claims, 3 Drawing Figures

EAR DEFENDERS

This invention relates to ear defenders, that is devices for protecting the wearer from excessive ambient noise. In situations of spasmodic noise it is desirable that the wearer can hear the voice of a nearby person, when he chooses, without having to remove the ear defender entirely. For this purpose, ear defenders have been provided which can be 'opened' to permit the passage of sound, by removal of a cap or operation of a valve. In one such ear defender a substantially rigid shell is provided having a mouth which (suitably padded) engages the head around the ear, the shell having a number of holes on a flat part opposite the ear. A valve is then mounted outside the shell to open and close these holes selectively. An acoustic impedance in the form of resilient pads, or spring members in conjunction with air spaces, may be arranged outside the valve again, in an attempt to give some desired frequency characteristic to the transmission of ambient sound through the valve to the wearer's ear.

While such arrangements, in which the valve and other features are mounted outside the shell, facilitate operation of the valve, the valve mechanism and any acoustic features are vulnerable to damage.

The external fitting of these features has a further disadvantage in that the telephone earpiece that is incorporated in the ear defender is normally fitted from inside the shell and thus assembly of the device is complicated by the necessity of access to both sides of the shell.

An object of the present invention is therefore to provide an ear defender which at least partially avoids the above difficulties.

According to the present invention, an ear defender comprises a shell of substantially rigid material adapted to enclose a space around a wearer's ear, at least one hole in said shell to permit the transmission of sound through the shell, and a valve mechanism mounted inside the shell and adapted to open and close selectively a path within the shell between said hole and the mouth of the shell, the valve mechanism being operable from outside the shell to permit the wearer to accept or reject sound waves from the ambient air.

The valve mechanism preferably comprises a plate having one or more holes and a shutter having one or more holes, the shutter being slidable against the plate to bring the holes in the plate and the shutter into and out of register selectively.

The shutter may be slidable linearly against the plate and have an arm attached, which extends through the shell for manual operation of the shutter.

A membrane is preferably positioned adjacent the inner face of the shell in the region of the hole in the shell to prevent the entry of foreign matter to the valve mechanism.

The earpiece unit may be spaced from the plate by a resilient element, the plate being retained in position against the shell at least partly by pressure from the resilient element.

An ear defender in accordance with the invention will now be described, by way of example, with reference to the accompanying drawings, of which:

Figure 1:
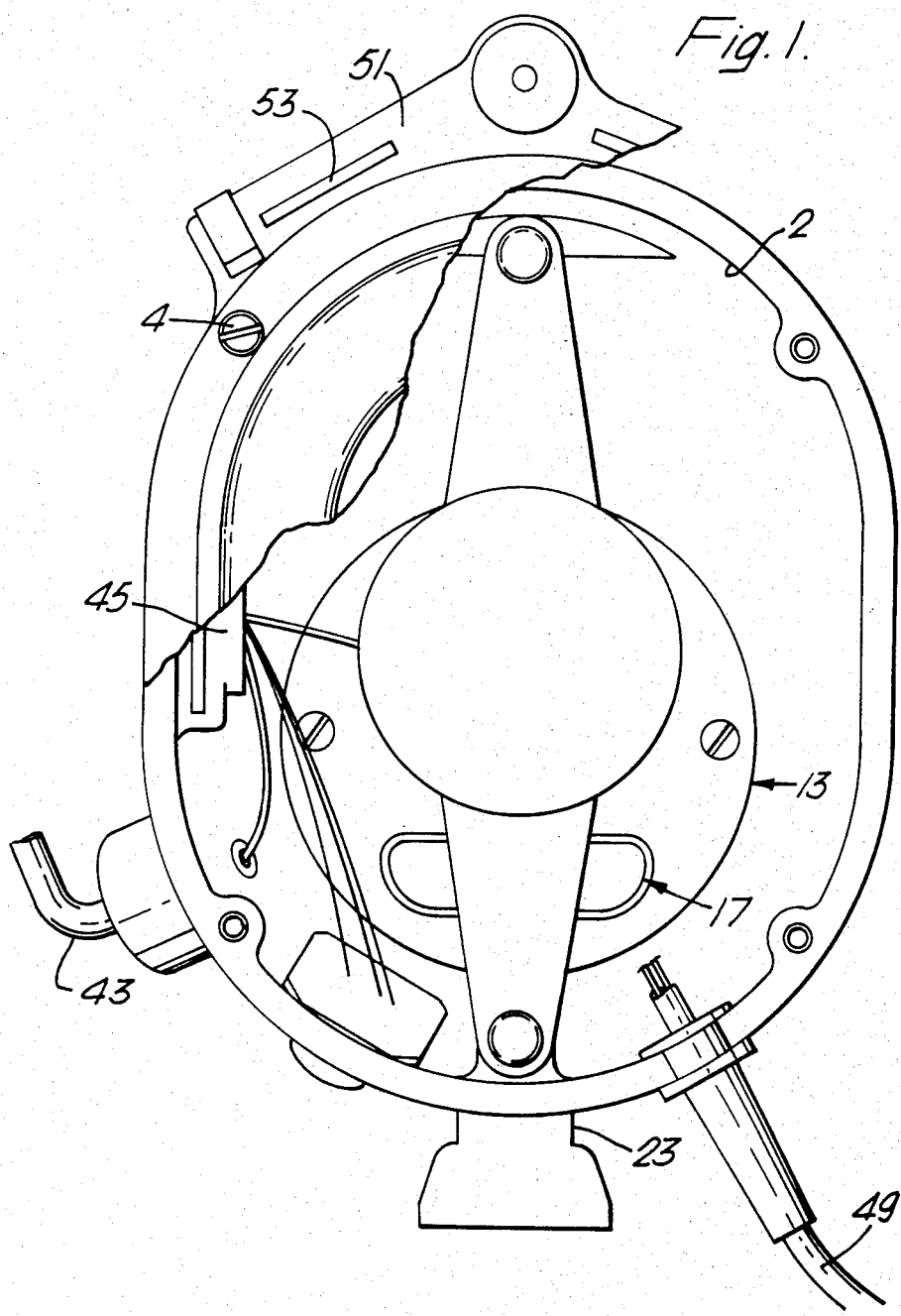
FIG. 1 is a partly broken away inside view of the ear defender.

Referring to the drawings, the ear defender consists basically of a substantially rigid shell 1, the open mouth 2 of which is screwed (at positions 4) on to an end plate 3 shown broken away in FIG. 1. The end plate 3 has a central aperture 5, rather smaller than the mouth of the shell, providing access to the wearer's ear. Around the aperture 5 is fixed a soft pad 7 which bears against the wearer's head in use, sealing the shell to the ear and normally excluding ambient sound.

Figure 2:
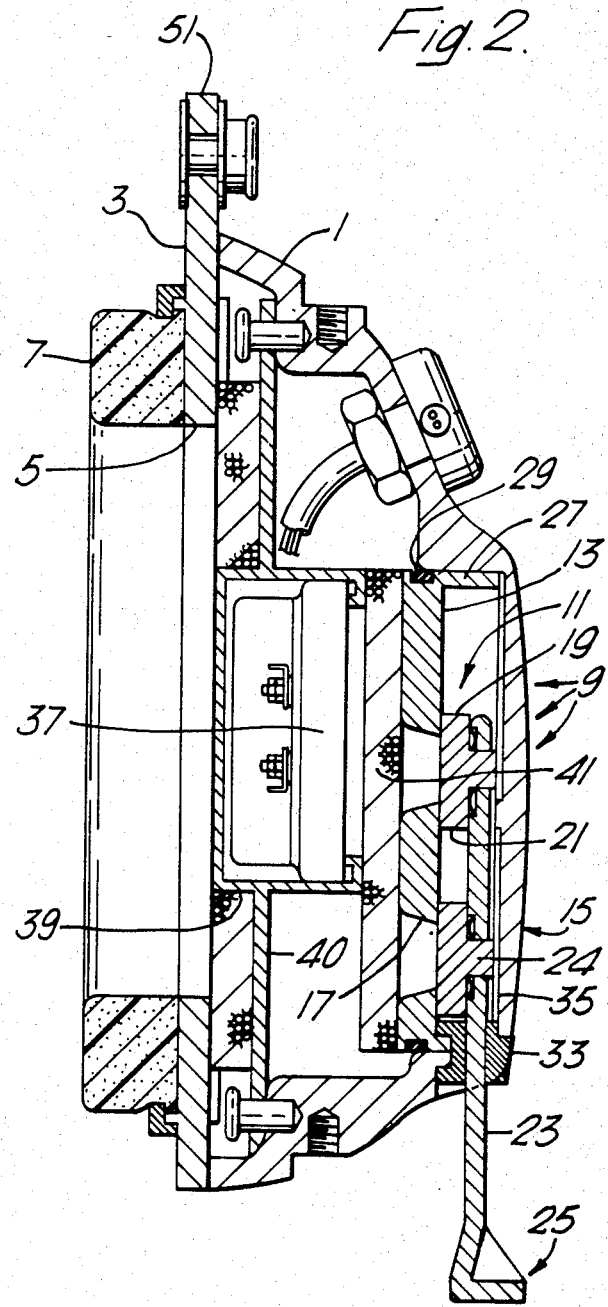
FIG. 2 is a cross sectional view on the line II—II of FIG. 3.
Figure 3:
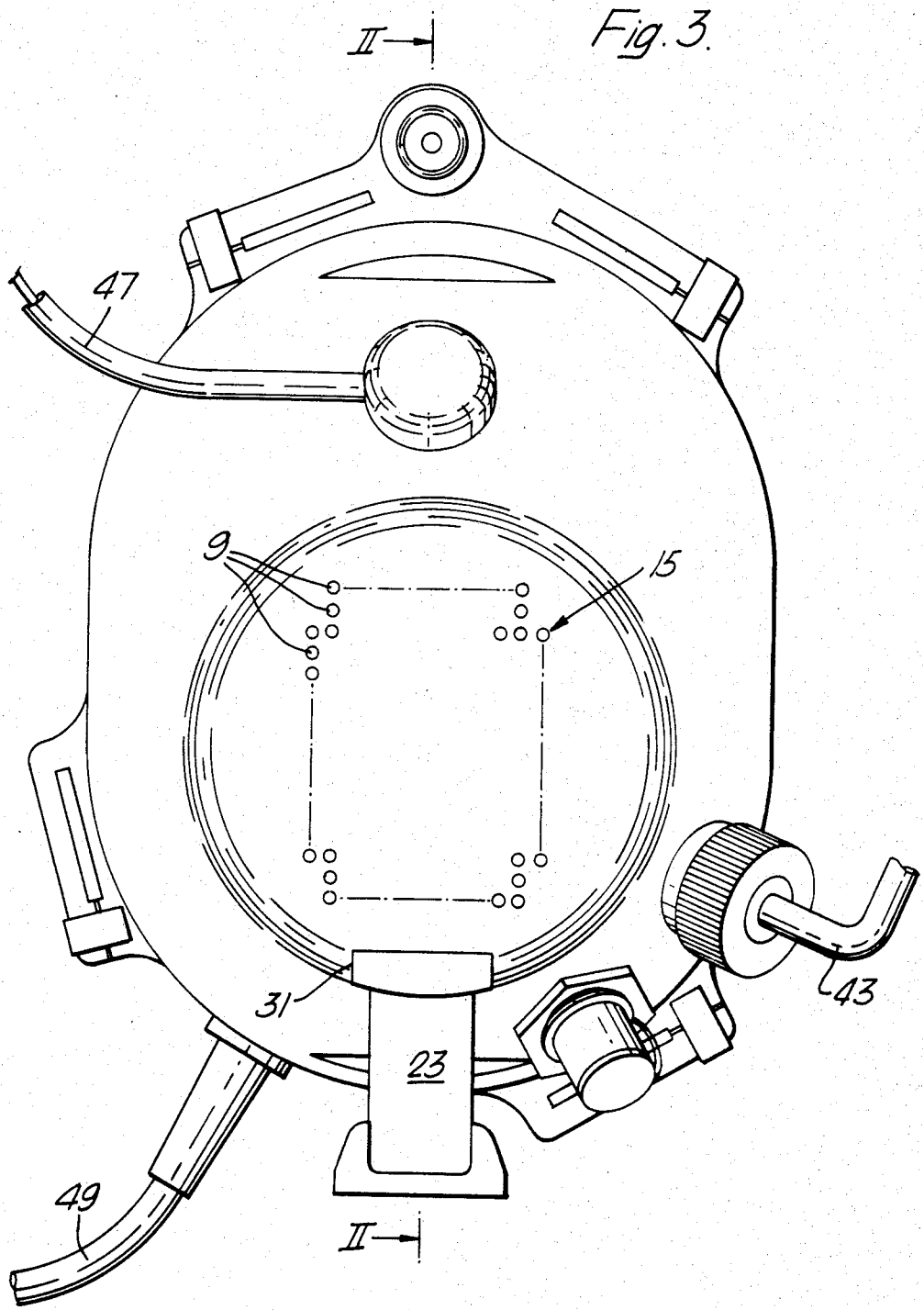
FIG. 3 is an outside view of the ear defender.

The part 15 of the shell 1 opposite the mouth, is provided with a large number of holes 9, shown in FIG. 3, to permit the entry of ambient sound to the ear. A valve mechanism 11 mounted inside the shell adjacent to the holes 9 permits selective opening and closing of the path within the shell between the holes 9 and the mouth 2. The valve mechanism comprises a shutter plate 13 mounted so as to close off the holed portion 15 of the shell from the remainder of the shell interior. A path through the plate 13 is then provided by two large holes 17 shown in section in FIG. 2 and one of which is visible in FIG. 1. A shutter 19 consists of a flat rectangular member which slides vertically (in the drawings) between the shutter plate 13 and the portion 15 of the shell, being urged against the plate 13 by wave washers.

The shutter 19 has a central hole 21 of the same extent as the holes 17 in the plate 13 and by sliding the shutter upwards (see FIG. 2) this hole 21 can be aligned with the upper hole 17. In the downward position of the shutter 19, as shown in FIG. 2, the hole 21 is out of register with upper hole 17 in the plate 13 and no passage for sound is provided.

The lower hole 17 in the plate 13 is obstructed by the lower part of the shutter 19 in the downward position but is open through the space below the lower edge of the shutter 19 in its upward position.

Control of the shutter 19 is effected by an arm 23 which protrudes through the edge of the shell 1 and engages two bosses 24 on the back face of the shutter 19. The arm 23 has a flat hooked formation 25 at its outer end to facilitate pulling and pushing by the wearer.

The plate 13 is to some extent cup-shaped, having a shallow surrounding wall 27 which beds into a corresponding recess on the inside surface of the shell 1. The transmission of sound around the edge of the plate 13 is then prevented by an 'O-ring' 29 fitted in a groove in the edge of the plate 13.

Assembly of the arm 23 is by means of a side entry 31 in the shell which is then closed by an insert 33. First the arm 23 is loosely fitted with the insert 33 and then inserted through the side entry 31. The shutter 19 is placed in position with its two bosses 24 engaging holes in the arm 23, and the insert 33 is then slid along the arm to engage the shell in the side entry 31. Insertion of the plate 13 then causes a cut away part of the wall 27 to engage and trap an insert 33.

Between the shell portion 15 and the valve mechanism a membrane 35 is trapped so preventing dust and noisture affecting the various components.

A telephone earpiece 37 is mounted in a container 39 which has arms 40 extending to mounting bosses on the shell. The arms are there attached by screws. Between the telephone earpiece 37 and the plate 13 a piece of resilient foam material 41 is positioned. This serves the double purpose of retaining the plate 13 in position and providing an acoustic impedance.

A microphone arm 43 is provided on one of a pair of ear defenders with connections made to a terminal block 45. A lead 47 provides a connection to the other telephone earpiece and overall connections to a telephone set are taken through a lead 49.

Extension portions 51 of the end plate 3 are provided with slots 53 for the attachment of straps.

In operation, in noisy conditions, the wearer keeps the arm 23 pulled down, i.e. as illustrated, so closing the valve mechanism and rejecting excessive ambient noises. If it is desired to listen to ambient sounds, a colleague talking perhaps, the wearer pushes up the arm 23 so opening the valve mechanism and accepting ambient sounds.

I claim:

1. An ear defender comprising a shell of substantially rigid material for enclosing a space around a wearer's ear, at least one hole in said shell to permit the transmission of sound through the shell, and a valve mechanism mounted inside the shell and operable to open and close selectively a path within the shell between said hole and the mouth of the shell, the valve mechanism being operable from outside the shell to permit the wearer to accept or reject sound waves from the ambient air, said valve mechanism comprising a plate having one or more holes and a shutter having one or more holes, the shutter being slidable against said plate to bring the holes in the plate and the shutter into and out of register selectively, said shutter being slidable linearly against said plate and has an arm attached, which extends through said shell for manual operation of the shutter.

2. An ear defender comprising a shell of substantially rigid material for enclosing a space around a wearer's ear, at least one hole in said shell to permit the transmission of sound through the shell, and a valve mechanism mounted inside the shell and operable to open and close selectively a path within the shell between said hole and the mouth of the shell, the valve mechanism being operable from outside the shell to permit the wearer to accept or reject sound waves from the ambient air, said valve mechanism comprising a plate having one or more holes and a shutter having one or more holes, the shutter being slidable against said plate to bring the holes in the plate and the shutter into and out of register selectively, a telephone earpiece unit mounted between said valve mechanism and the mouth of the shell, said telephone earpiece unit being spaced from said plate by a resilient element, said plate being retained in position against the shell at least partly by pressure from the resilient element.

* * * * *